(12) United States Patent
Beaulieu et al.

(10) Patent No.: US 8,664,009 B2
(45) Date of Patent: Mar. 4, 2014

(54) ARSENICAL FLUORESCENT AGENTS AND ASSAYS

(75) Inventors: Laura Ellen Downs Beaulieu, Menlo Park, CA (US); Mary J. Tanga, Menlo Park, CA (US)

(73) Assignee: SRI International, Menlo Park, CA (US)

( * ) Notice: Subject to any disclaimer, the term of this patent is extended or adjusted under 35 U.S.C. 154(b) by 399 days.

(21) Appl. No.: 13/053,206

(22) Filed: Mar. 21, 2011

(65) Prior Publication Data

US 2011/0229929 A1 Sep. 22, 2011

Related U.S. Application Data

(60) Provisional application No. 61/315,723, filed on Mar. 19, 2010.

(51) Int. Cl.
*G01N 33/533* (2006.01)
*G01N 21/76* (2006.01)
*G01N 33/20* (2006.01)

(52) U.S. Cl.
USPC .............................. 436/546; 436/172; 436/73

(58) Field of Classification Search
None
See application file for complete search history.

(56) References Cited

U.S. PATENT DOCUMENTS

| | | | |
|---|---|---|---|
| 6,451,569 B1 * | 9/2002 | Tsien et al. | 435/174 |
| 6,831,160 B1 * | 12/2004 | Vale et al. | 530/412 |
| 7,381,572 B2 * | 6/2008 | Ebright et al. | 436/546 |
| 2005/0176065 A1 * | 8/2005 | Hanson | 435/7.1 |
| 2006/0141531 A1 * | 6/2006 | Ebright et al. | 435/7.1 |

\* cited by examiner

*Primary Examiner* — Shafiqul Haq
(74) *Attorney, Agent, or Firm* — Richard Aron Osman

(57) ABSTRACT

The invention provides methods and compositions for labeling dithiol-containing analytes.

19 Claims, No Drawings

ARSENICAL FLUORESCENT AGENTS AND ASSAYS

This application claims priority to U.S. 61/315,723 filed Mar. 19, 2010.

BACKGROUND OF THE INVENTION

The field of the invention is arsenical fluorescent agents and diagnostic assays.

Neglected Tropical Diseases (NTDs) are a group of infections that most commonly plague those who are extremely poor and live in remote rural areas, urban slums, and places of political conflict. Because they adversely affect child development, pregnancy, and worker productivity, NTDs are a major reason why many in developing nations cannot escape extreme poverty. Three such diseases are caused by trypanosomal parasites: Chagas' disease, African Trypanosomiasis or Sleeping Sickness, and Leishmaniasis.

While these diseases manifest in several clinical forms they are caused by a family of parasites with conserved biochemical machinery. We have exploited these similarities to develop a new diagnostic to be administered at the point of care (POC). In the case of these NTDs, the POC can be anywhere from a remote village along the Amazon to a forward operating base in Iraq. Thus, POC diagnostics must perform well in low technology settings with minimal requisite technical training. Since rapid and accurate diagnosis is critical for any disease control strategy, new diagnostics for these diseases are needed for better identification and monitoring of treatment populations.

There are two classes of diagnostics for these diseases: (1) parasitological methods that detect the parasite directly; these typically require observation of the parasite in blood samples under a microscope, and are labor intensive, time consuming, and are often inadequate for diagnosis in the chronic phase of infection when parasite levels in the blood are lower; and (2) immunological methods that rely on detection of markers from a patient's immune response; these methods are very sensitive but require highly trained technicians and expensive technology making them impractical for a field setting.

We have developed a new parasitological method that eliminates the need for trained personnel and expensive instrumentation, instead using a highly specific molecular sensor that can be detected with a handheld UV lamp or black light.

Immobilized monoarsenical [aminohexanoyl-4-aminophenylarsineoxide] supports have been described [Kalef et al., Anal Biochem. 1993 Aug. 1; 212(2):325-34; Kalef et al., Methods Enzymol. 1994, 233, 395-403] for the purification of proteins, and Adams et al., (J. Am. Chem. Soc., 2002, 124 (21), pp 6063-6076, 6068, col. 2, line 5) describes a a fluorescein with just one arsenic substituent, 4'-(1,3,2-dithiarsolan-2-yl)-5-carboxyfluorescein; see also, Hoffman et al., Nat. Protoc. 2010 September; 5(10):1666-77. Epub 2010 Sep. 23, "Fluorescent labeling of tetracysteine-tagged proteins in intact cells.".

SUMMARY OF THE INVENTION

The invention provides methods and compositions for labeling dithiol-containing analytes. In one embodiment, the invention provides a substituted, optionally hydro-, optionally hetero-, monoarsenical anthracene compound comprising a 4' rotation blocking group and a 5' arsenic, and that exhibits a detectable increase or shift in fluorescence when the arsenic reacts with two thiols of a rotation-blocking binding target molecule, the compound having the structure I:

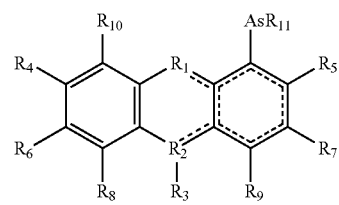

wherein:

R1 is O, S, NRα, or CRα$_2$;

R2 is C or N;

R3 is optionally substituted-, optionally hetero-alkyl, optionally substituted-, optionally hetero-alkenyl, optionally substituted-, optionally hetero-alkynyl, optionally substituted-, optionally hetero-aryl, or optionally substituted-, optionally hetero-alkoxy;

R4 and R5 are independently carbonyl, carbonothioyl, NRα$_2$, ORα, or SRα;

R6 and R7 are Rα, halide, ORα, NRα$_2$, ORα, SRα, or nitro (—NO$_2$);

R8 and R9 are Rα, halide, ORα, NRα$_2$, ORα, SRα, or nitro (—NO$_2$);

R10 is a rotational blocking group;

R11 is an arsenic protecting group displaced by reaction of the arsenic with the thiols of the target molecule;

Rα groups are independently H, optionally substituted-, optionally hetero-alkyl, optionally substituted-, optionally hetero-alkenyl, optionally substituted-, optionally hetero-alkynyl, optionally substituted-, optionally hetero-aryl, or optionally substituted-, optionally hetero-alkoxy;

wherein one or more of the pairs R4-R6, R6-R8, R5-R7, and R7-R9 may be covalently joined in one or more rings;

and tautomers, anhydrides and salts of the compound.

The invention encompasses all combinations of disclosed particular embodiments thereof, including wherein: R11 is carbonyl, 1,2 ethanedithiol, or dihydroxyl, the rotation blocking group is an optionally substituted-, optionally hetero-alkyl, optionally substituted-, optionally hetero-alkenyl, optionally substituted-, optionally hetero-alkynyl, optionally substituted-, optionally hetero-aryl, or optionally substituted-, optionally hetero-alkoxy, and or the anthracene compound is a fluoresein, rhodamine, eosin, phenazine, phenoxazine, phenothiazine, thioxanthene, acridine, or a core or derivative thereof.

In a more general embodiment, the invention provides a substituted, optionally hydro-, optionally hetero-, monoarsenical anthracene compound comprising a 4' rotation-blocking group and a 5' arsenic, and that exhibits a detectable increase or shift in fluorescence when the arsenic reacts with two thiols of a rotation-blocking binding target molecule forming a conjugate having the general structure II:

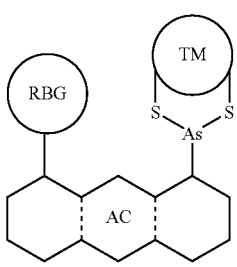

wherein AC is the anthracene core, RB is the rotation blocking group and TM is the target molecule, and tautomers, anhydrides and salts of the compound.

The invention also provide methods of making and using the subject compounds, including a method of using a subject compound comprising the step of: contacting the compound with the target molecule wherein the arsenic reacts with the thiols, and in particular, a method of diagnosing a trypanasomatid infection in a patient by detecting a dicysteine trypanathione, comprising the steps of: (a) contacting a sample of the patient with a subject compound; and (b) detecting the increase or shift in fluorescence as an indication of the presence of the trypanathione and the trypanasomatid infection.

The invention also provides a method of diagnosing a trypanasomatid infection in a patient by detecting a dicysteine trypanathione, comprising the steps of: (a) contacting a sample of the patient with an arsenical fluorescent dye that exhibits a detectable increase or shift in fluorescence when the arsenic of the dye reacts with the cysteines of the trypanathione; and (b) detecting the increase or shift in fluorescence as an indication of the presence of the trypanathione and the trypanasomatid infection.

The subject monoarsenical dyes have a significant advantage over diarsenical dyes in diagnoses, in that they form a brightly fluorescent complex upon binding of a dicysteine motif, whereas he 1:1 complex with prior diarsenical dyes is only weakly fluorescent. This in not a flaw of the diarsenicals, but reflect their distinct design criteria. Biarsenicals are used in excess to track a small concentration of proteins as they are trafficked through cells, and hence require exquisite selectivity and high binding affinity afforded by the tetradentate binding capacity of the bisarsenical. Essentially, the biarsenticals were engineered as a small molecule equivalent of GFP to monitor protein trafficking. In contrast, our diagnostic goals required a probe much more sensitive, and the duration of binding event is not as critical. Accurate diagnosis needs to detect a metabolite with two proximal cysteines selectively, and employing a monoarsenical means that a 1:1 binding stoichiometry can provide a fluorescent conjugate which is more favorable in this context. Furthermore, use of the blocking group allows the binding event to provide a much brighter conjugate since free rotation about the arsenic carbon bond is more hindered and therefore fluorescence is less quenched.

In addition the invention provides all recombinations of alternative recited elements as if each recombination were separately set forth.

DETAILED DESCRIPTION OF SPECIFIC EMBODIMENTS OF THE INVENTION

The invention provides a substituted, optionally hydro-, optionally hetero-, monoarsenical anthracene compound comprising a 4' rotation-blocking group and a 5' arsenic, and that exhibits a detectable increase or shift in fluorescence when the arsenic reacts with two thiols of a rotation-blocking binding target molecule forming a conjugate having the general structure II:

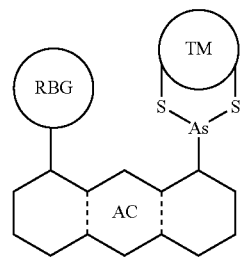

wherein AC is the anthracene core, RB is the rotation blocking group and TM is the target molecule, and tautomers, anhydrides and salts of the compound.

In a more specific embodiment of Structure II, the invention provides a substituted, optionally hydro-, optionally hetero-, monoarsenical anthracene compound comprising a 4' rotation blocking group and a 5' arsenic, and that exhibits a detectable increase or shift in fluorescence when the arsenic reacts with two thiols of a rotation-blocking binding target molecule, the compound having the structure I:

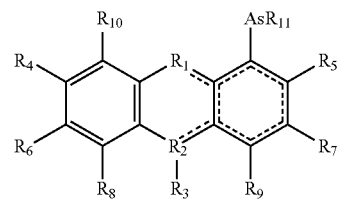

wherein:
R1 is O, S, NRα, or CRα$_2$;
R2 is C or N;
R3 is optionally substituted-, optionally hetero-alkyl, optionally substituted-, optionally hetero-alkenyl, optionally substituted-, optionally hetero-alkynyl, optionally substituted-, optionally hetero-aryl, or optionally substituted-, optionally hetero-alkoxy;
R4 and R5 are independently carbonyl, carbonothioyl, NRα$_2$, ORα, or SRα;
R6 and R7 are Rα, halide, ORα, NRα$_2$, ORα, SRα, or nitro (—NO$_2$);
R8 and R9 are Rα, halide, ORα, NRα$_2$, ORα, SRα, or nitro (—NO$_2$);
R10 is a rotational blocking group;
R11 is an arsenic protecting group displaced by reaction of the arsenic with the thiols of the target molecule;
Rα groups are independently H, optionally substituted-, optionally hetero-alkyl, optionally substituted-, optionally hetero-alkenyl, optionally substituted-, optionally hetero-alkynyl, optionally substituted-, optionally hetero-aryl, or optionally substituted-, optionally hetero-alkoxy;
wherein one or more of the pairs R4-R6, R6-R8, R5-R7, and R7-R9 may be covalently joined in one or more rings;
and tautomers, anhydrides and salts of the compound.

The following descriptions of particular embodiments and examples are provided by way of illustration and not by way of limitation. Those skilled in the art will readily recognize a variety of noncritical parameters that could be changed or modified to yield essentially similar results. Unless contraindicated or noted otherwise, in these descriptions and throughout this specification, the terms "a" and "an" mean one or more, the term "or" means and/or and polynucleotide sequences are understood to encompass opposite strands as well as alternative backbones described herein. Furthermore, genuses are recited as shorthand for a recitation of all members of the genus; for example, the recitation of (C1-C3) alkyl is shorthand for a recitation of all C1-C3 alkyls: methyl, ethyl and propyl, including isomers thereof.

The term "heteroatom" as used herein generally means any atom other than carbon, hydrogen or oxygen. Preferred heteroatoms include oxygen (O), phosphorus (P), sulfur (S), nitrogen (N), silicon (S), arsenic (As), selenium (Se), and halogens, and preferred heteroatom functional groups are haloformyl, hydroxyl, aldehyde, amine, azo, carboxyl, cyanyl, thocyanyl, carbonyl, halo, hydroperoxyl, imine, aldimine, isocyanide, iscyante, nitrate, nitrile, nitrite, nitro, nitroso, phosphate, phosphono, sulfide, sulfonyl, sulfo, and sulfhydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —CH$_2$—CH$_2$—CH$_2$—CH$_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si (CH$_3$)$_3$, —CH$_2$—CH=N—OCH$_3$, and —CH=CH—N (CH$_3$)—CH$_3$. Up to two heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent means a divalent radical derived from heteroalkyl, as exemplified by —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5, 6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C1-C4)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR", —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —CN and —NO$_2$, in a number ranging from zero to three, with those groups having zero, one or two substituents being particularly preferred. R', R" and R'" each independently refer to hydrogen, unsubstituted (C1-C8)alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R'", —OC(O)R', —C(O)R', —CO$_2$R', —CONR'R", —OC(O)NR'R", —NR"C(O)R', —NR"CO$_2$R', —NR'—SO$_2$NR"R", —S(O)R', —SO$_2$R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R'", —SO$_2$R', —SO$_2$NR'R", —NR"SO$_2$R, —CN and —NO$_2$.

Similarly, substituents for the aryl and heteroaryl groups are varied and selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO2R', —NR'—C(O)NR"R'", —NR'—SO$_2$NR"R'", —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —N$_3$, —CH(Ph)$_2$, perfluoro(C1-C4)alko-xy and perfluoro(C1-C4)alkyl, in a number ranging from zero to the total number of open valences on the aromatic ring system; and where R', R" and R'" are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl". Typically, an aryl or heteroaryl group will have from zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —S(O)R', —SO$_2$R', —SO$_2$NR'R", —NR"SO$_2$R, —N$_3$, —CH(Ph)$_2$, perfluoro(C1-C4)alkoxy and perfluoro(C1-C4)alkyl, where R' and R" are as defined above. Further preferred substituents are selected from: halogen, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R, perfluoro(C1-C4)alkoxy and perfluoro(C1-C4)alkyl.

The substituent —CO$_2$H, as used herein, includes bioisosteric replacements therefor; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)r-B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)s-X—(CH$_2$)t-, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C1-C6)alkyl.

In both embodiments, the rotation blocking group (RBC or R10) is bulky group that limits rotation of the substituent at the 4' carbon of anthracene ring core sufficient to substantially reduce fluorescent quenching. A proton (H), F, or other small, or small, linear substituents are insufficiently bulky to quench fluorescence, as is the —AsEDT group of the biarsenicals discussed below. Preferred blocking groups are large, bulky, tetrahedral, and/or aryl functional groups, particularly optionally substituted-, optionally hetero-alkyl, optionally substituted-, optionally hetero-alkenyl, optionally substituted-, optionally hetero-alkynyl, optionally substituted-, optionally hetero-aryl, or optionally substituted-, optionally hetero-alkoxy.

What is important is that the blocking group quench the fluorescence of the compound sufficiently so that when the arcenic atom binds the thiols of the binding target, a practically detectable increase or shift in fluorescence results. Without being bound by the theory, the idea is that when the metabolite binds, there is more bulk about the arsenic carbon bond. If there is a substituent in the 4'/5' position, the newly formed ring system will be very bulky and its free rotation will be prevented by the presence of that blocking group. When you limit free rotation, you decrease the efficiency of the quenching process, effectively unquenching the fluorescnce. In practice synthetic accessibility, convenience, resultant chemical and fluorometric properties, and compatibility with the intended binding target assay effectively guide the selection the blocking group. Accordingly, the target molecule, when bound to the compound though a pair of thiols, such as a dicysteine, similarly inhibits rotation at the 5' carbon (note that the 4' and 5' positions can be reversed, depending on the tautomer) of anthracene ring core sufficient to substantially reduce fluorescent quenching.

The 5' arsenic atom is typically protected with an arsenic protecting group (R11) displaced by reaction of the arsenic with the thiols of the target molecule. This protecting group should be fluorescent quenching (should not limit free rotation), and is hence, preferably a relatively small, non-bulky group like carbonyl or dihydroxyl, and particularly, small dithiols like 1,2 ethanedithiol. What is important is that target binding provides a detectable increase or shift in fluorescence compared with the protecting group (e.g. EDT)-bound As. The protecting groups may be used to protect the arsenical molecule from reacting with low affinity sites. Dithiol protecting groups may form a five- or six-membered ring with the arsenic. Vicinal dithiols that form rings, such as 5-membered rings, are preferable. Dithiols that contain rings may increase the affinity of the dithiol to the arsenic by organizing the two thiol groups to be in a cis-conformation ready to form an additional ring with the arsenic. Examples of dithiol rings are 1,2 benzenedithiol and 1,2-cyclohexanedithiol. Preferably, the arsenic is bonded to a dithiol, such as 1,2-ethanedithiol (EDT).

The subject compounds encompass the core structures of a wide variety of anthracene-based fluorescent molecules including fluorescein, rhodamine, eosin, phenazine, phenoxazine, phenothiazine, thioxanthene, acridine, and cores and derivatives thereof. A wide variety of such anthracene cores are commercially available or readily synthesized by those skilled in the art. For example, Sigma-Aldrich lists dozens of fluoresceins and derivatives:

| Product# | Description |
| --- | --- |
| 07217 | 1-(O'-Methylfluorosceinyl)piperidine-4-carboxylic acid |
| 35845 | 2',7'-Dichlorofluorescein diacetate |
| C7153 | 5(6)-Carboxyfluorescein Mixed isomers |
| C8166 | 5(6)-Carboxyfluorescein diacetate Mixed isomers |
| 21888 | 5(6)-Carboxyfluorescein diacetate N-succinimidyl ester |
| D0531 | 5-([4,6-Dichlorotriazin-2-yl]amino)fluorescein hydrochloride |
| 72755 | 5-(Bromomethyl)fluorescein |
| I9271 | 5-(Iodoacetamido)fluorescein |
| 87444 | 5-Carboxy-fluorescein diacetate N-succinimidyl ester |
| 86826 | 5-Carboxyfluorescein |
| 92846 | 5-Carboxyfluorescein N-succinimidyl ester |
| D9908 | 6-([4,6-Dichlorotriazin-2-yl]amino)fluorescein hydrochloride |
| C4109 | 6-Carboxy-4',5'-dichloro-2',7'-dimethoxyfluorescein N-hydroxysuccinimide ester |
| 08951 | 6-Carboxy-fluorescein diacetate N-succinimidyl ester |
| C0662 | 6-Carboxyfluorescein |
| 54115 | 6-Carboxyfluorescein |
| 46935 | 6-[Fluorescein-5(6)-carboxamido]hexanoic acid |
| 46940 | 6-[Fluorescein-5(6)-carboxamido]hexanoic acid N-hydroxysuccinimide ester |
| E6003 | Eosin Y disodium salt |
| E4382 | Eosin Y disodium salt |
| 32617 | Eosin Y disodium salt |
| 45240 | Eosin Y disodium salt |
| 318906 | Eosin Y solution |
| F2456 | Fluorescein (free acid) |
| F3651 | Fluorescein 5(6)-isothiocyanate |
| 46950 | Fluorescein 5(6)-isothiocyanate |
| 46939 | Fluorescein diacetate 5-maleimide |
| 36438 | Fluorescein diacetate 6-isothiocyanate |
| F7250 | Fluorescein isothiocyanate isomer I |
| F4274 | Fluorescein isothiocyanate isomer I |
| 46951 | Fluorescein isothiocyanate isomer I |
| F2502 | Fluorescein isothiocyanate isomer I |
| 46980 | Fluorescein mercuric acetate |
| 28803 | Fluorescein sodium salt |
| 46970 | Fluorescein sodium salt |
| F9551 | Fluorescein-5-EX N-hydroxysuccinimide ester |
| 88596 | Fluorescein-O'-acetic acid |
| 07294 | O'-(Carboxymethyl)fluoresceinamide |

Generating other suitable anthracene derivatives is a mature art, with well-established protocols, e.g. Hermanson, 2008, Bioconjugate techniques (Academic Press, 2008); Afonso et al., Chem. Soc. Rev., 2009, 38, 2410-2433 "Synthesis and applications of Rhodamine derivatives as fluorescent probes", Jose et al. Tetrahedron 62 (2006) 11021-11037, "Benzophenoxazine-based fluorescent dyes for labeling biomolecules".

The subject compounds encompass monoarsenical forms of the biarsenical compounds disclosed in U.S. Pat. No. 7,776,999, U.S. Pat. No. 7,524,972, U.S. Pat. No. 7,138,503, U.S. Pat. No. 6,900,304, U.S. Pat. No. 6,686,458, U.S. Pat. No. 6,451,569, U.S. Pat. No. 6,054,271, U.S. Pat. No. 6,008,378, U.S. Pat. No. 5,932,474, wherein the 4' arsenical group of the biarsenical is replaced with a 4' rotation blocking group as disclosed herein, and the compound provides the request fluorescence and binding.

For subject diagnostic assay use, the anthracene is initially selected for its optical properties, and may be optimized according to the following criteria: (1) ability to form a fluorescent conjugate with a single molecule of TSH2; (2) brightness of the monoarsenical-TSH2 conjugate; (3) wavelength of absorption ($\lambda$abs) and the wavelength of emission ($\lambda$ems); (4) resistance to photobleaching; and (5) rate of conjugation with TSH2. Any monoarsenical dye that has $\lambda$0.5% of the fluorescence of the monoarsenical-TSH2 conjugate, forms a bright complex in a short time period, and has a maximum $\lambda$abs in the UVA range (320-400 nm, the optical range of a commercially available black light) should be confirmed for use and compatibility in serum extracts.

In particular embodiments the compounds encompass:

| fluoresein-based compounds wherein: | phenothiazine-based compounds wherein: |
|---|---|
| R1 is O; | R1 is S; |
| R2 is C; | R2 is N; |
| R3 is 2-carboxyphenyl; | R3 is H or C; |
| R4 is hydroxyl; | R4 is hydroxyl; |
| R5 is carbonyl; | R5 is carbonyl; |
| R6 and R7 are H; and | R6 and R7 are H; and |
| R8 and R9 are H. | R8 and R9 are H |
| fluoresein-based compounds wherein: | thioxanthene-based compounds wherein: |
| R1 is O; | R1 is S; |
| R2 is C; | R2 is C; |
| R3 is 2-carboxyphenyl; | R3 is 2-carboxyphenyl; |
| R4 is hydroxyl; | R4 is hydroxyl; |
| R5 is carbonyl; | R5 is carbonyl; |
| R6 and R7 are H or Cl; | R6 and R7 are H; and |
| R8 and R9 are H; and | R8 and R9 are H. |
| R10 is methyl or benzyl | |
| rhodamine-based compounds wherein: | anthracene-based compounds wherein: |
| R1 is O; | R1 and R2 are C; |
| R2 is C; | R3 is H or C; |
| R3 is 2-carboxyphenyl; | R4 and R5 are O, S, N; |
| R4 is amine; | R6 and R7 are H; and |
| R5 is amine; | R8 and R9 are H. |
| R6 and R7 are H; and | |
| R8 and R9 are H | |
| eosin-based compounds wherein: | acridine-based compounds wherein: |
| R1 is O; | R1 is N; |
| R2 is C; | R2 is C; |
| R3 is 2-carboxyphenyl; | R3 is H or C; |
| R4 is hydroxyl; | R4 and R5 are O, S, or N; |
| R5 is carbonyl; | R6 and R7 are H; and |
| R6 and R7 are Br or nitro (—$NO_2$); and | R8 and R9 are H. |
| R8 and R9 are H. | |
| phenazine-based compounds wherein: | acridine yellow (2,7-Dimethylacridine-3,6-diamine)-based compounds wherein: |
| R1 and R2 are N; | R1 is N; |
| R3 is H or methyl; | R2 is C; |
| R4 and R5 are O, S, or N; | R3 is H; |
| R6 and R7 are H; and | R4 and R5 are $NH_2$; |
| R8 and R9 are H | R6 and R7 are $CH_3$; and |
| | R8 and R9 are H |
| phenoxazine-based compounds wherein: | acridine orange (N,N,N',N'-Tetramethylacridine-3,6-diamine)-based compounds wherein: |
| R1 is O; | R1 is N; |
| R2 is N; | R2 is C; |
| R3 is H or methyl; | R3 is H; |
| R4 is hydroxyl; | R4 and R5 are $N(CH_3)_2$; |
| R5 is carbonyl; | R6 and R7 are H; and |
| R6 and R7 are H; and | R8 and R9 are H. |
| R8 and R9 are H. | |

An exemplary synthetic scheme and exemplary compounds 1-4 are shown below.

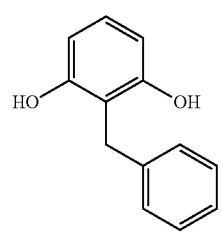 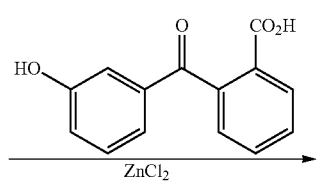

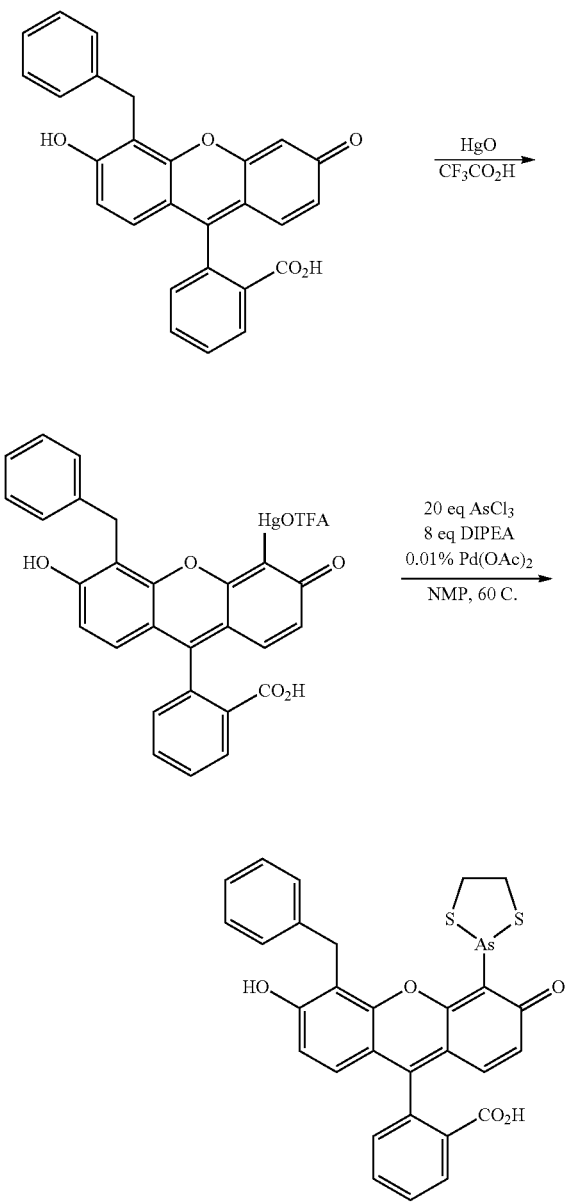

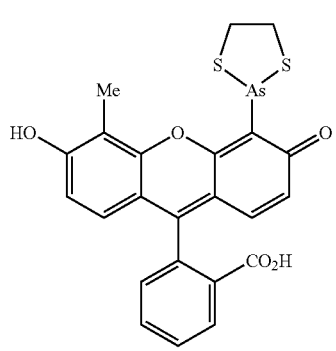

1

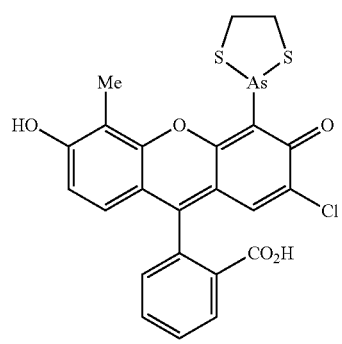

2

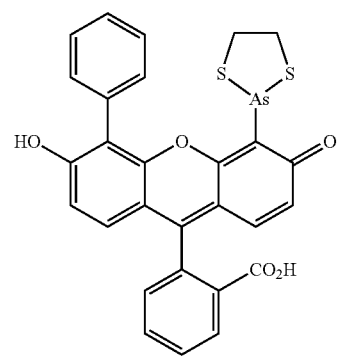

3

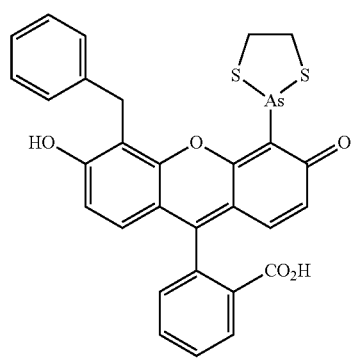

4

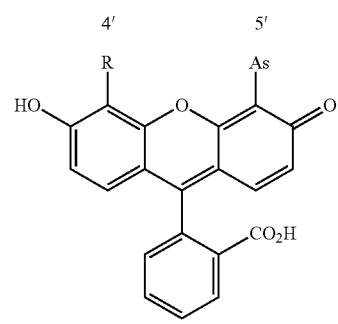

The invention encompasses tautomers, anhydrides and salts of the subject compounds. For example, a generic 4'-5' tautomer is shown here:

1

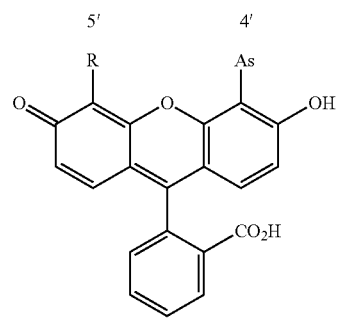

Furthermore, the structures below show two tautomers of compound 5 as well as its salt form. In addition, one can hydrolyze to get the hydrate or dehydrate to get the arsenic oxide Compound 8 is the biotin conjugate, which may be used for example, in the construction of solid supported dyes for use in the diagnostic.

1

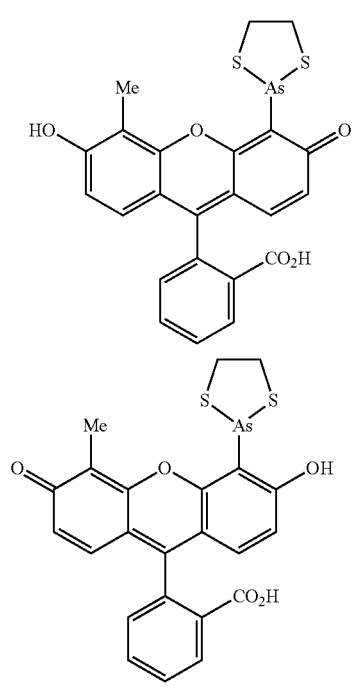

Tautomers

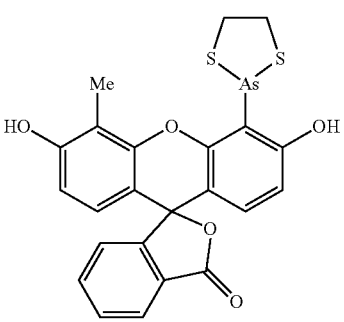

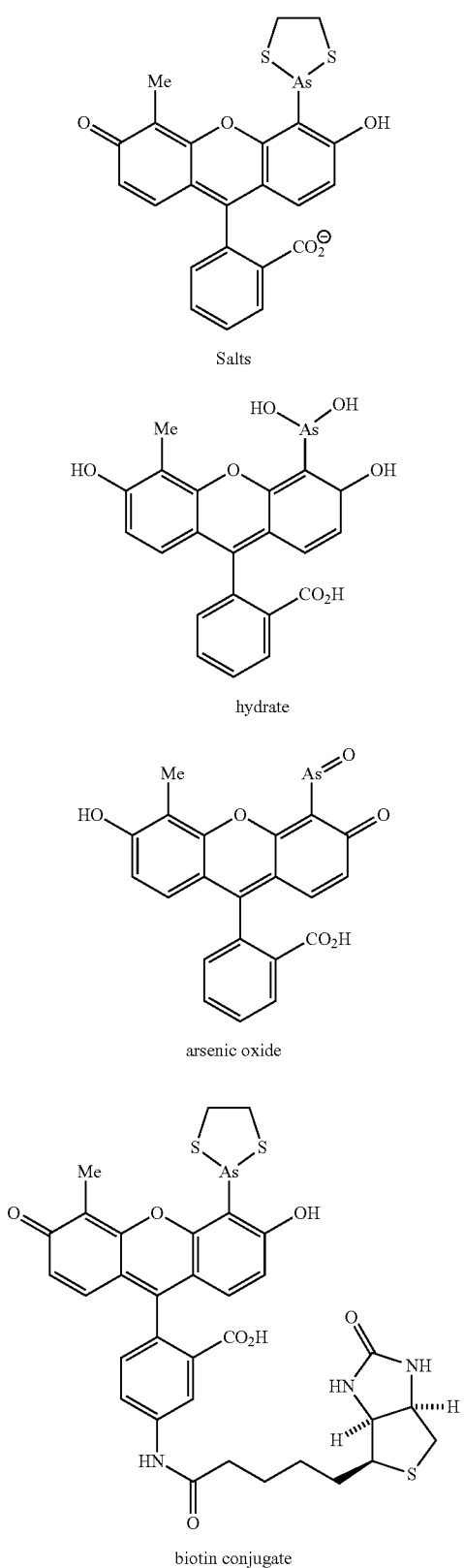

Salts hydrate arsenic oxide biotin conjugate

The invention also encompasses method of making the subject compounds and conjugates, and methods of using the subject compounds comprising the step of: (a) contacting the compound with the target molecule wherein the arsenic reacts with the thiols, and particularly, a dicysteine. In a more particular embodiment, the invention provides a method of diagnosing a trypanasomatid infection in a patient by detecting a dicysteine trypanathione, comprising the steps of: (a) contacting a sample of the patient with a subject compound; and (b) detecting the increase or shift, particularly a red-shift, in fluorescence as an indication of the presence of the trypanathione and the trypanasomatid infection.

In a separate embodiment, the invention provides a method of diagnosing a trypanasomatid infection in a patient by detecting a dicysteine trypanathione, comprising the steps of: (a) contacting a sample of the patient with an arsenical fluorescent dye that exhibits a detectable increase or shift in fluorescence when the arsenic of the dye reacts with the cysteines of the trypanathione; and (b) detecting the increase or shift in fluorescence as an indication of the presence of the trypanathione and the trypanasomatid infection. This embodiment provides and encompasses a novel and unprecedented use of prior art biarsenicals.

EXAMPLES

Trypanosomal parasites regulate the oxidative environment inside their cells using a unique redox pair, the metabolite trypanothione ($TSH_2$,) and the enzyme trypanothione reductase (TyR). $TSH_2$ was first described as the potential target for arsenical therapeutics used to treat these infections. This pathway is orthogonal to that of glutathione and glutathione reductase (GR) found in the human patient or other mammals. Since the arsenical therapeutics have such a high affinity for the sulfur atoms in $TSH_2$, we hypothesized that arsenical dyes could be sensitive and selective sensors for the detection of trypanosomal parasites.

To test this hypothesis, we employed the fluorescein arsenical helix binder ($FlAsH-EDT_2$) dye first developed by Roger Tsien and coworkers for the in vivo imaging of peptides and proteins possessing four cysteine amino acids. When unbound, $FlAsH-EDT_2$ is virtually non-fluorescent. Upon binding of four sulfur atoms, free rotation about the As—C bond is restricted, and the dye becomes brightly fluorescent. Since this visualization method labels proteins inside of cells with low background fluorescence, we hypothesized that this molecular sensor could detect the parasite metabolite without interference from other thiols present in biological fluids. The binding of two molecules of $TSH_2$ should prevent the free rotation about the As—C bond in FlAsH, causing a fluorimetric response.

$FlAsH-EDT_2$ was virtually non-fluorescent, but upon introduction of $TSH_2$, the fluorescence intensity rose. After approximately 10 minutes, the reaction reached saturation. Using the normalized fluorescence measurements, we found that $FlAsH-EDT_2$ had 0.4% of the fluorescence of the FlAsH-$(TSH_2)_2$ conjugate. The excitation and emission maxima for the conjugate were 505 nm and 527 nm respectively. This increase in fluorescence is readily detectable without a fluorimeter using a simple handheld black light such as those used at airport security checkpoints. This detection method could be implemented easily in a low technology, resource poor setting. We examined the limits of detection of the metabolite with $FlAsH-EDT_2$. In our liquid-liquid method, a 10-fold excess of the metabolite is sufficient to observe a fluorimetric response within twenty minutes. Therefore, 2.5 nmol of the dye can be used to detect 25 nmol of the metabolite. While lower concentrations were detectable using a fluorimeter, the conjugation was too slow to be practical. However, $FlAsH-EDT_2$ was not designed and is not optimized for this purpose, and it requires two molecules of TSH$_2$ to bind in order to achieve the desired fluorescence response.

Hence we developed next generation dyes that have better optical properties and faster development times upon binding TSH$_2$. We focused our efforts on the synthesis of a monoarsenical probe for the detection of TSH$_2$. We hypothesized that if we could replace one of the sensor domains with a bulky group, binding of TSH$_2$ to the single sensor domain would restrict free rotation and cause a fluorimetric response. This hypothesis was verified. We synthesized a panel of dyes, which possesses a single arsenic nucleus and has a blocking group (such as a methyl group) to prevent free rotation about the As—C bond. Indeed, conjugation of TSH$_2$ provides a measureable on response. There are a number of features that make our monoarsenicals better for a trypanosomal diagnostic than FlAsH-EDT$_2$; for example, our dyes only requires a single metabolite to bind in order to obtain the desired fluorimetric response decreasing both the amount of dye required to detect the metabolite and the time required for detection. This dramatic improvement translates to a better POC device.

To optimize the optical properties of our target dye, we initially synthesized a library of monoarsenical dyes from fluorescein and rhodamine scaffolds. Fluorescein, a well-studied imaging agent that has been approved by the FDA, has strong fluorescence at low pH values and is the basis for FlAsH-EDT$_2$ and SRI-010346. Rhodamine dyes have more favorable properties for our diagnostic purposes. Compared with fluorescein, they are relatively resistant to photobleaching and are fluorescent over a broad pH range of 4-10. Our data indicate the broad applicability of our monoarsenicals to trypanosome diagnosis.

Scheme 2: Synthetic approach to ew monoarsenical dyes with different optical properties.

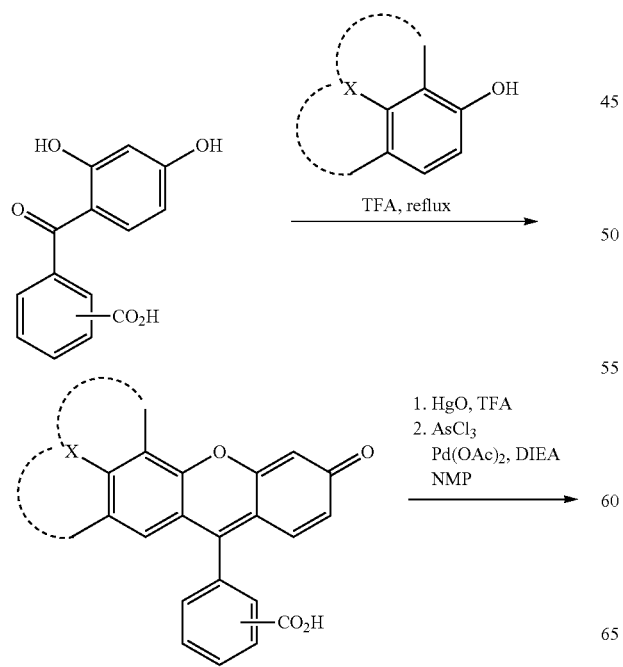

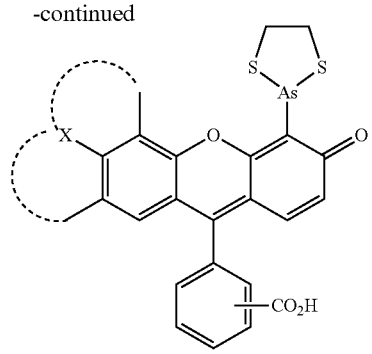

The invention encompasses all recombinations of alternative elements or components as if each recombination were individually and belaboredly set forth herein. The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims

What is claimed is:

1. A method of diagnosing a trypanasomatid infection in a patient by detecting a dicysteine trypanathione, comprising the steps of:
   (a) contacting a sample of the patient with an arsenical fluorescent dye that exhibits a detectable increase or shift in fluorescence when the arsenic of the dye reacts with the cysteines of the trypanathione; and
   (b) detecting the increase or shift in fluorescence as an indication of the presence of the trypanathione and the trypanasomatid infection;
   wherein the dye is a substituted, optionally hydro-, optionally hetero-, monoarsenical anthracene compound comprising a 4' rotation blocking group and a 5' arsenic, and that exhibits a detectable increase or shift in fluorescence when the arsenic reacts with two thiols of a rotation-blocking binding target molecule, the compound having the structure I:

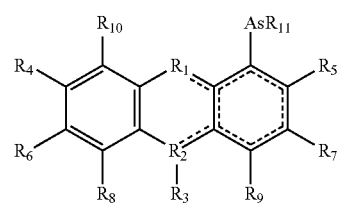

wherein:
   R1 is O, S, NRα, or CRα$_2$;
   R2 is C or N;
   R3 is optionally substituted-, optionally hetero-alkyl, optionally substituted-, optionally hetero-alkenyl, optionally substituted-, optionally hetero-alkynyl, optionally substituted-, optionally hetero-aryl, or optionally substituted-, optionally hetero-alkoxy;

R4 and R5 are independently carbonyl, carbonothioyl, $NR\alpha_2$, $OR\alpha$, or $SR\alpha$;

R6 and R7 are $R\alpha$, halide, $OR\alpha$, $NR\alpha_2$, $OR\alpha$, $SR\alpha$, or nitro ($-NO_2$);

R8 and R9 are $R\alpha$, halide, $OR\alpha$, $NR\alpha_2$, $OR\alpha$, $SR\alpha$, or nitro ($-NO_2$);

R10 is a rotational blocking group;

R11 is an arsenic protecting group displaced by reaction of the arsenic with the thiols of the target molecule;

$R\alpha$ groups are independently H, optionally substituted-, optionally hetero-alkyl, optionally substituted-, optionally hetero-alkenyl, optionally substituted-, optionally hetero-alkynyl, optionally substituted-, optionally hetero-aryl, or optionally substituted-, optionally hetero-alkoxy;

wherein one or more of the pairs R4-R6, R6-R8, R5-R7, and R7-R9 may be covalently joined in one or more rings;

and tautomers, anhydrides and salts of the compound.

2. The method of claim 1 wherein R11 is carbonyl, 1,2 ethanedithiol, or dihydroxyl.

3. The method of claim 1 wherein the rotation blocking group is an optionally substituted-, optionally hetero-alkyl, optionally substituted-, optionally hetero-alkenyl, optionally substituted-, optionally hetero-alkynyl, optionally substituted-, optionally hetero-aryl, or optionally substituted-, optionally hetero-alkoxy.

4. The method of claim 1 wherein:
R1 is O;
R2 is C;
R3 is 2-carboxyphenyl;
R4 is hydroxyl;
R5 is carbonyl;
R6 and R7 are H; and
R8 and R9 are H.

5. The method of claim 1 wherein:
R1 is O;
R2 is C;
R3 is 2-carboxyphenyl;
R4 is hydroxyl;
R5 is carbonyl;
R6 and R7 are H or Cl;
R8 and R9 are H; and
R10 is methyl or benzyl.

6. The method of claim 1 wherein:
R1 is O;
R2 is C;
R3 is 2-carboxyphenyl;
R4 is amine;
R5 is amine;
R6 and R7 are H; and
R8 and R9 are H.

7. The method of claim 1 wherein:
R1 is O;
R2 is C;
R3 is 2-carboxyphenyl;
R4 is hydroxyl;
R5 is carbonyl;
R6 and R7 are Br or nitro ($-NO_2$); and
R8 and R9 are H.

8. The method of claim 1 wherein:
R1 and R2 are N;
R3 is H or methyl;
R4 and R5 are O, S, or N;
R6 and R7 are H; and
R8 and R9 are H.

9. The method of claim 1 wherein:
R1 is O;
R2 is N;
R3 is H or methyl;
R4 is hydroxyl;
R5 is carbonyl;
R6 and R7 are H; and
R8 and R9 are H.

10. The method of claim 1 wherein:
R1 is S;
R2 is N;
R3 is H or C;
R4 is hydroxyl;
R5 is carbonyl;
R6 and R7 are H; and
R8 and R9 are H.

11. The method of claim 1 wherein:
R1 is S;
R2 is C;
R3 is 2-carboxyphenyl;
R4 is hydroxyl;
R5 is carbonyl;
R6 and R7 are H; and
R8 and R9 are H.

12. The method of claim 1 wherein:
R1 and R2 are C;
R3 is H or C;
R4 and R5 are O, S, N;
R6 and R7 are H; and
R8 and R9 are H.

13. The method of claim 1 wherein:
R1 is N;
R2 is C;
R3 is H or C;
R4 and R5 are O, S, or N;
R6 and R7 are H; and
R8 and R9 are H.

14. The method of claim 1 wherein:
R1 is N;
R2 is C;
R3 is H;
R4 and R5 are $NH_2$;
R6 and R7 are $CH_3$; and
R8 and R9 are H.

15. The method of claim 1 wherein:
R1 is N;
R2 is C;
R3 is H;
R4 and R5 are $N(CH_3)_2$;
R6 and R7 are H; and
R8 and R9 are H.

16. The method of claim 1 wherein the compound is selected from:

21
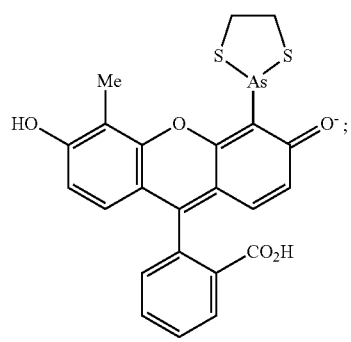
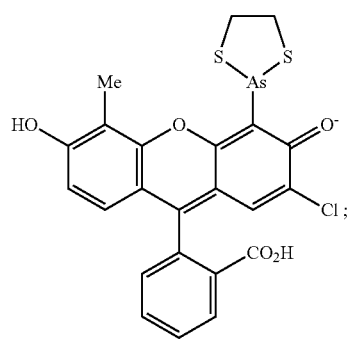
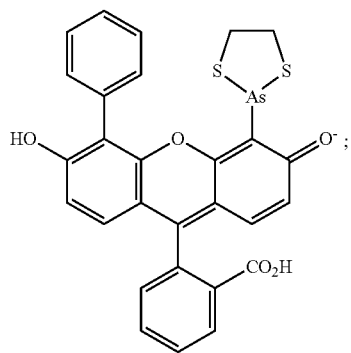
22
-continued
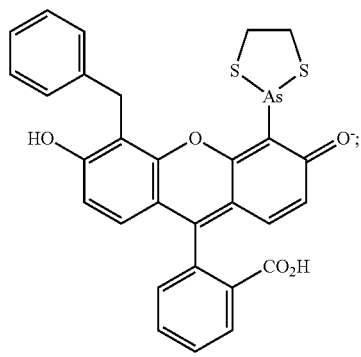
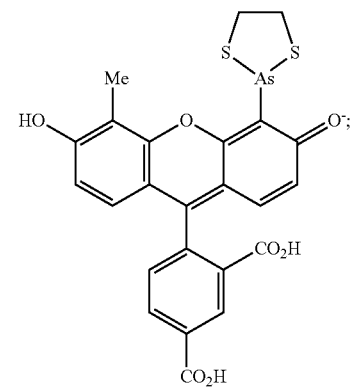
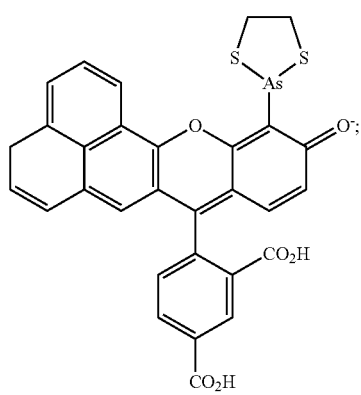
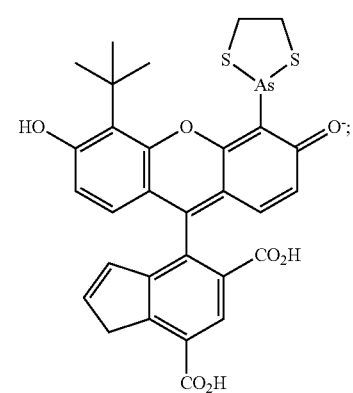

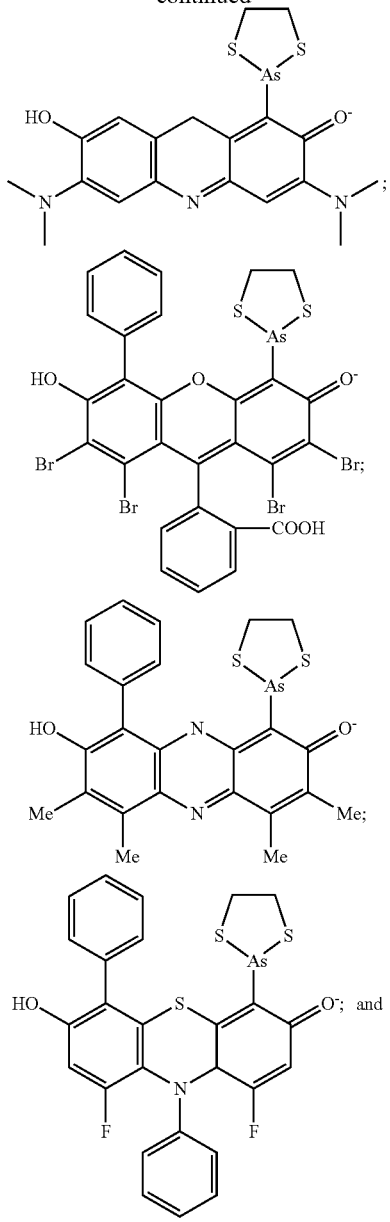

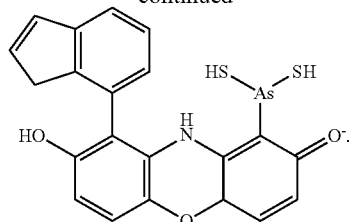

17. The method of claim 1 wherein the dye is a substituted, optionally hydro-, optionally hetero-, monoarsenical anthracene compound comprising a 4' rotation-blocking group and a 5' arsenic, and that exhibits a detectable increase or shift in fluorescence when the arsenic reacts with two thiols of a rotation-blocking binding target molecule forming a conjugate having the general structure II:

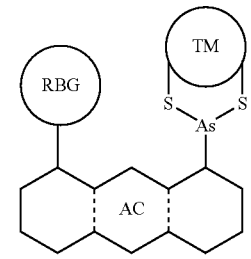

wherein AC is the anthracene core, RB is the rotation blocking group and TM is the target molecule, and tautomers, anhydrides and salts of the compound.

18. The method of claim 4 wherein the rotation blocking group is an optionally substituted-, optionally hetero-alkyl, optionally substituted-, optionally hetero-alkenyl, optionally substituted-, optionally hetero-alkynyl, optionally substituted-, optionally hetero-aryl, or optionally substituted-, optionally hetero-alkoxy.

19. The method of claim 5 wherein R11 is carbonyl, 1,2 ethanedithiol, or dihydroxyl.

* * * * *